US012221745B2

(12) United States Patent
Banach et al.

(10) Patent No.: US 12,221,745 B2
(45) Date of Patent: Feb. 11, 2025

(54) METHODS OF USING A PHENOLIC FATTY ACID COMPOUND ON A SYNTHETIC FABRIC MATERIAL

(71) Applicant: SI GROUP, INC., The Woodlands, TX (US)

(72) Inventors: Timothy Edward Banach, Scotia, NY (US); Gary Robideau, Niskayuna, NY (US); L. Scott Howard, Ballston Spa, NY (US); Gennaro Barbiero, Niskayuna, NY (US)

(73) Assignee: SI GROUP, INC., The Woodlands, TX (US)

( * ) Notice: Subject to any disclaimer, the term of this patent is extended or adjusted under 35 U.S.C. 154(b) by 1 day.

(21) Appl. No.: 17/842,333

(22) Filed: Jun. 16, 2022

(65) Prior Publication Data

US 2022/0403586 A1 Dec. 22, 2022

Related U.S. Application Data

(63) Continuation of application No. 15/125,534, filed as application No. PCT/US2015/020530 on Mar. 13, 2015, now Pat. No. 11,390,987.

(60) Provisional application No. 61/953,462, filed on Mar. 14, 2014.

(51) Int. Cl.
*D06M 13/207* (2006.01)
*C07C 51/367* (2006.01)
*C08J 5/04* (2006.01)
*C08J 5/06* (2006.01)
*D01F 1/10* (2006.01)
*D06M 13/152* (2006.01)
*D06M 15/37* (2006.01)
*D06M 15/693* (2006.01)

(52) U.S. Cl.
CPC ......... *D06M 13/207* (2013.01); *C07C 51/367* (2013.01); *C08J 5/046* (2013.01); *C08J 5/06* (2013.01); *D01F 1/10* (2013.01); *D06M 13/152* (2013.01); *D06M 15/37* (2013.01); *D06M 15/693* (2013.01); *C08J 2321/00* (2013.01); *C08J 2321/02* (2013.01); *C08J 2461/12* (2013.01); *D06M 2400/01* (2013.01); *D10B 2101/06* (2013.01)

(58) Field of Classification Search
None
See application file for complete search history.

(56) References Cited

U.S. PATENT DOCUMENTS

| 2,374,576 | A | | 4/1945 | Merlin et al. |
| 3,458,449 | A | * | 7/1969 | Katstra ............... C07C 303/44 252/384 |
| 5,380,789 | A | | 1/1995 | Nanaumi et al. |
| 2006/0169408 | A1 | | 8/2006 | Rutherford et al. |

FOREIGN PATENT DOCUMENTS

| EP | 1837364 | * | 3/2006 |
| JP | S50-65691 | | 6/1975 |
| JP | S59-124920 | | 7/1984 |
| JP | S60210616 | * | 10/1985 |
| JP | H05-194905 | | 8/1993 |
| JP | H105-194905 | | 8/1993 |
| JP | H06-65340 | | 3/1994 |
| JP | H06-256447 | | 9/1994 |
| JP | H0948833 | * | 2/1997 |
| JP | S63-295508 | | 12/1998 |
| JP | 2005-511904 | | 4/2005 |

OTHER PUBLICATIONS

Machine Translation of JPS60210616 (Year: 1985).*
Machine Translation of JPH0948833 (Year: 1997).*

* cited by examiner

*Primary Examiner* — Shawn Mckinnon
(74) *Attorney, Agent, or Firm* — Jeffrey N. Townes; Cozen O'Connor

(57) ABSTRACT

This invention relates to a process for making phenolic fatty acid compounds having a reduced phenolic ester content. The invention also relates to method for chemically bonding a phenolic resin with a non-phenolic polymer (e.g., a synthetic fabric). The method comprises contacting a phenolic fatty acid compound with a non-phenolic polymer to introduce a hydroxy phenyl functional group into the non-phenolic polymer; and reacting the hydroxy phenyl functional group contained in the non-phenolic polymer with a phenolic resin or a phenolic crosslinker composition capable of forming a phenolic resin, to chemically bond the phenolic resin with the non-phenolic polymer. The invention is particularly useful for making a synthetic fabric-reinforced article, such as synthetic fabric-reinforced rubber article, circuit board substrate, or fiberglass.

22 Claims, No Drawings

METHODS OF USING A PHENOLIC FATTY ACID COMPOUND ON A SYNTHETIC FABRIC MATERIAL

This application is a continuation of U.S. application Ser. No. 15/125,534, filed Sep. 12, 2016, which is a 35 U.S.C. § 371 National-Stage application of International PCT Application No. PCT/2015/020530, filed Mar. 12, 2015, which claims priority to U.S. Provisional Application No. 61/953,462, filed on Mar. 14, 2014, all of which are herein incorporated herein by reference in their entirety.

FIELD OF THE INVENTION

This invention generally relates to a process for making phenolic fatty acid compounds and using the resulting phenolic fatty acid compounds to chemically bond a phenolic resin with a non-phenolic polymer, e.g., a fabric material. This invention is particularly useful for making a synthetic fabric-reinforced article.

BACKGROUND

Fabric-reinforced polymer materials are a category of composite materials that use fabric materials to mechanically enhance the strength and elasticity of the polymer materials. For example, rubber articles such as tires, hoses, and belts are composite materials of various natural and synthetic rubber compositions reinforced with different reinforcing materials such as reinforced fibers made from synthetic fabric materials.

When forming the composite materials, it is desirable to achieve good adhesion between the reinforcing fabric phase and the polymer matrix phase (i.e., the polymer material without fabric reinforcement) to maintain the integrity of the composite material. However synthetic fabrics have difficulty of adhering to the polymer matrix because of their generally smooth polymer surfaces and low surface activity, typically because of their lower polarity and reactivity of the polymer molecules in the fabric material.

To promote the adhesion between the reinforcing fabric phase and the polymer matrix phase, much of the current technology employs adhesives and related applying processes. For example, two adhesive systems are widely used to promote the adhesion between the reinforcing fabric fiber and the rubber compositions in tire industry: the resorcinol-formaldehyde-latex (RFL) coating method where an RFL adhesive is applied to the fabric cord, and the hexamethylenetetramine-resorcinol or hexamethoxymethylmelamine-resorcinol adhesion promoting methods in which an adhesion promotion system is incorporated into the rubber composition.

However, none of the existing technology sufficiently establishes a chemical bonding between the fabric phase and the phenolic adhesive to promote the strong adhesion between the fabric phase and the polymer matrix phase. Therefore, there remains a need in the art to develop an improved method to achieve a better adhesion between the reinforcing fabric phase and the polymer matrix phase. A particular need exists in the rubber industry to provide an improved bonding between the reinforced fabric material and the rubber composition. This invention answers that need.

SUMMARY OF THE INVENTION

One aspect of the invention relates to a process for making a phenolic fatty acid compound having a reduced phenolic ester content. The method comprises providing a fatty acid composition comprising at least one unsaturated fatty acid, and reacting a phenolic compound with the fatty acid composition in the presence of an acidic catalyst at a temperature ranging from about 90° C. to about 120° C. to form the phenolic fatty acid compound. The method produces a phenolic fatty acid compound with less than 5 wt % phenolic ester.

Another aspect of the invention relates to a method for chemically bonding a phenolic resin with a non-phenolic polymer. The method comprises contacting a phenolic fatty acid compound with a non-phenolic polymer having a functional group reactive to a carboxylic acid group of a fatty acid, to react the carboxylic acid-reactive functional group of the non-phenolic polymer with the carboxylic acid group of the phenolic fatty acid compound, thereby attaching a hydroxy phenyl functional group to the non-phenolic polymer. The method further comprises reacting the hydroxy phenyl functional group of the non-phenolic polymer with a phenolic resin or a phenolic crosslinker composition capable of forming a phenolic resin, to chemically bond the phenolic resin with the non-phenolic polymer.

Another aspect of the invention relates to a method for chemically bonding a phenolic resin with a synthetic fabric material. The method comprises contacting a phenolic fatty acid compound with a synthetic fabric material to introduce a hydroxy phenyl functional group into the synthetic fabric material. The method further comprises reacting the hydroxy phenyl functional group contained in the synthetic fabric material with a phenolic resin or a phenolic crosslinker composition capable of forming a phenolic resin, to chemically bond the phenolic resin with the synthetic fabric material.

Another aspect of the invention relates to a synthetic-fabric reinforced rubber composition. The composition comprises a rubber composition and a synthetic fabric phase. The synthetic fabric phase has been (a) modified by a phenolic fatty acid compound to contain a hydroxy phenyl functional group, and (b) coated with a phenolic resin, wherein the synthetic fabric phase and the coated phenolic resin are chemically bonded through the hydroxy phenyl functional group. The synthetic fabric phase is used as reinforced materials for the rubber composition.

Another aspect of the invention relates to a synthetic-fabric reinforced article. The article comprises an article containing a phenolic resin, and a synthetic fabric phase. The synthetic fabric phase is modified by a phenolic fatty acid compound to contain a hydroxy phenyl functional group. The synthetic fabric phase and the article are chemically bonded through the hydroxy phenyl functional group. The article can be a rubber composition, a circuit board substrate, or a fiberglass.

Additional aspects, advantages and features of the invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of the stated aspects, advantages and features make up the inventions disclosed in this application.

DETAILED DESCRIPTION OF THE INVENTION

This invention relates to a process for making phenolic fatty acid compounds and using the resulting phenolic fatty acid compounds to chemically bond a phenolic resin with a non-phenolic polymer, e.g., a fabric material. The non-phenolic polymer (e.g., a synthetic fabric) typically does not react, or reacts only minimally, with the phenolic resin, without the presence of the phenolic fatty acid compound. The method takes advantage of the bi-functionality of the phenolic fatty acid compound, i.e., the carboxylic acid functionality and the hydroxy phenyl functionality, to chemically bond the non-phenolic polymer phase and the phenolic resin phase. This invention is particularly useful for making a synthetic fabric-reinforced article, such as synthetic fabric-reinforced rubber article, circuit board substrate, or fiberglass.

Process of Making a Phenolic Fatty Acid Compound

One aspect of the invention relates to a process for making a phenolic fatty acid compound having a reduced phenolic ester content. The method comprises providing a fatty acid composition comprising at least one unsaturated fatty acid, and reacting a phenolic compound with the fatty acid composition in the presence of an acidic catalyst at a temperature ranging from about 90° C. to about 120° C. to form the phenolic fatty acid compound. The method produces a phenolic fatty acid compound with less than 5 wt % phenolic ester.

The phenolic compound may be a monohydric, dihydric, or polyhydric phenol. Suitable monohydric, dihydric, or polyhydric phenols include, but are not limited to, phenol; dihydricphenols such as resorcinol, catechol, and hydroquinone; dihydroxybiphenol; alkylidenebisphenols such as 4,4'-methylenediphenol (bisphenol F), and 4,4'-isopropylidenediphenol (bisphenol A); trihydroxybiphenol; and thiobisphenols. The benzene ring of the monohydric, dihydric, or polyhydric phenols can be substituted in the ortho, meta, and/or para positions by one or more linear, branched, or cyclic $C_1$-$C_{30}$ alkyl, or halogen (F, Cl, or Br). For example, the benzene ring can be substituted by $C_1$-$C_{16}$ alkyl, $C_1$-$C_6$ alkyl, or $C_1$-$C_4$ alkyl. Suitable substituents on the benzene ring also include $C_1$-$C_{30}$ aralkyl, $C_1$-$C_{30}$ alkanoyl, and $C_1$-$C_{30}$ aroyl. Exemplary phenolic compounds include phenol or resorcinol; or phenol or resorcinol substituted with one or more methyl groups, such as cresol, xylenol, or methyl resorcinol.

The fatty acid composition can come from any natural oils or fats, or processed source of fatty acids that provide one or more unsaturated fatty acids. Suitable oils include, but are not limited to, a variety of vegetable oils such as soybean oil, peanut oil, walnut oil, palm oil, palm kernel oil, wheat germ oil sesame oil, sunflower oil, safflower oil, rapeseed oil, linseed oil, flax seed oil, colza oil, coconut oil, corn oil, cottonseed oil, olive oil, castor oil, false flax oil, hemp oil, mustard oil, radish oil, ramtil oil, rice bran oil, salicornia oil, tigernut oil, tung oil, and mixtures thereof. Suitable fats include, but are not limited to, beef or mutton fat such as beef tallow or mutton tallow; pork fat such as pork lard; poultry fat such as turkey and/or chicken fat, or duck fat; and fish fat/oil. Typical fatty acid compositions used include commercially available oils or fats that contain a large amount of mixed unsaturated fatty acids, derived from, for instance, cotton, soy, linseed oil, or tall oil. The fatty acid composition may comprise one or more fatty acids listed in Table 1. Commercially available unsaturated fatty acids such as undecylenic acid, oleic acid, linoleic acid, linolenic acid, palmitoleic acid, and erucic acid, as well as isomeric modifications of these acids can also be used. An exemplary fatty acid composition comprises oleic acid, linoleic acid, linolenic acid, or mixtures thereof.

TABLE 1

Suitable unsaturated fatty acids for making a phenolic fatty acid compound

| Common name | Chemical structure | Property |
|---|---|---|
| Myristoleic acid | $CH_3(CH_2)_3CH=CH(CH_2)_7COOH$ | Unsaturated fatty acid with $C_{14}$ and one double bond |
| Palmitoleic acid | $CH_3(CH_2)_5CH=CH(CH_2)_7COOH$ | Unsaturated fatty acid with $C_{16}$ and one double bond |
| Sapienic acid | $CH_3(CH_2)_8CH=CH(CH_2)_4COOH$ | Unsaturated fatty acid with $C_{16}$ and one double bond |
| Oleic acid | $CH_3(CH_2)_7CH=CH(CH_2)_7COOH$ | Unsaturated fatty acid with $C_{18}$ and one double bond |
| Elaidic acid | $CH_3(CH_2)_7CH=CH(CH_2)_7COOH$ | Unsaturated fatty acid with $C_{18}$ and one double bond |
| Vaccenic acid | $CH_3(CH_2)_4CH=CH(CH)_{10}COOH$ | Unsaturated fatty acid with $C_{18}$ and one double bond |
| Elaidic acid | $CH_3(CH)_7CH=CH(CH_2)_7COOH$ | Unsaturated fatty acid with $C_{18}$ and one double bond |
| Vaccenic acid | $CH_3(CH2)_4CH=CH(CH_2)_{10}COOH$ | Unsaturated fatty acid with $C_{18}$ and one double bond |
| Linoleic acid | $CH_3(CH_2)_4CH=CHCH_2CH=CH(CH_2)_7COOH$ | Polyunsaturated fatty acid with $C_{18}$ and two double bonds |
| Linoelaidic acid | $CH_3(CH_2)_4CH=CHCH_2CH=CH(CH_2)_7COOH$ | Polyunsaturated fatty acid with $C_{18}$ and two double bonds |
| α-Linolenic acid | $CH_3CH_2CH=CHCH_2CH=CHCH_2CH=CH(CH_2)_7COOH$ | Polyunsaturated fatty acid with $C_{18}$ and three double bonds |

TABLE 1-continued

Suitable unsaturated fatty acids for making a phenolic fatty acid compound

| Common name | Chemical structure | Property |
|---|---|---|
| Arachidonic acid | $CH_3(CH_2)_4CH=CHCH_2CH=CHCH_2CH=CHCH_2CH=CH(CH_2)_3COOH$ | Polyunsaturated fatty acid with $C_{20}$ and four double bonds |
| Eicosapentaenoic acid | $CH_3CH_2CH=CHCH_2CH=CHCH_2CH=CHCH_2CH=CHCH_2CH=CH(CH_2)_3COOH$ | Polyunsaturated fatty acid with $C_{20}$ and five double bonds |
| Erucic acid | $CH_3(CH_2)_7CH=CH(CH_3)_{11}COOH$ | Unsaturated fatty acid with $C_{22}$ and one double bond |
| Docosahexaenoic acid | $CH_3CH_2CH=CHCH_2CH=CHCH_2CH=CHCH_2CH=CHCH_2CH=CHCH_2CH=CH(CH_2)_2COOH$ | Polyunsaturated fatty acid with $C_{22}$ and six double bonds |

The reaction of the phenolic compound with the fatty acid composition involves alkylation of the phenolic compound with the unsaturated fatty acid, in which the reaction occurs at the double bond of the fatty acid and adds the phenol benzene ring and a hydrogen atom to each unsaturated carbon atom of the double bond in the fatty acid. For example, a phenol stearic acid compound can be prepared from the reaction of oleic acid and phenol, with the primary reaction product being [9,10]-(hydroxyphenol)-octadecanoic acid), as shown in Scheme 1.

Scheme 1

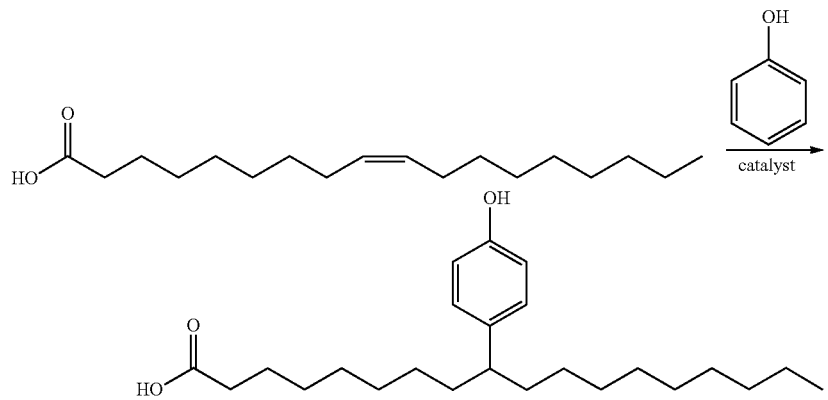

When a mixture of unsaturated fatty acids are present in the fatty acid composition, each unsaturated fatty acid can react with the phenolic compound, thereby forming a mixture of phenolic fatty acid compounds where the phenol benzene rings are alkylated with various fatty acids. When the fatty acid composition contains one or more polyunsaturated fatty acids, the reaction of the phenol benzene ring of the phenolic compound with the fatty acid may occur at one or more double bonds within the polyunsaturated fatty acid, i.e., the resulting phenolic fatty acid product may contain a mixture of a completely saturated aliphatic chain, and a partially saturated aliphatic chain. For example, when phenol reacts with linolenic acid, which contains two double bonds, the resulting phenolic fatty acid product may be phenol stearic acid (two double bonds are completely saturated by addition of the phenol benzene rings), phenolic oleic acid (only one double bond is saturated by addition of the phenol benzene ring, and another double bond is left unsaturated), or a mixture thereof. Exemplary reactions also include reacting phenol with palmitoleic acid or linolenic acid to form phenol palmitic acid or phenol behenic acid, respectively.

The reaction of the phenolic compound with the fatty acid composition can result a byproduct of phenolic ester, formed by the reaction of the hydroxyl group of the phenolic compound with the carboxyl group of the fatty acids. The resulting undesirable phenolic ester byproducts mix with the phenolic fatty acid product and cause coloration of the phenolic fatty acid product, which impairs the subsequent usage of the phenolic fatty acid product. To improve the effectiveness of alkylation of the phenolic compound with the unsaturated fatty acid, reduce the esterification byproduct, and decolor the phenolic fatty acid product, the reaction is carried out in the presence of an acidic catalyst at a temperature ranging from about 90° C. to about 120° C. This low reaction temperature can significantly reduce the formation of phenolic ester byproducts.

Suitable acidic catalysts include, but are not limited to, sulfuric acid, ethanesulfonic acid, benzenesulfonic acid, benzenedisulfonic acid, chlorobenzenesulfonic acid, 3,4-dichlorobenzene sulfonic acid, cresolsulfonic acids, phenol sulfonic acids, toluenesulfonic acids, xylenesulfonic acids, octylphenolsulfonic acid, naphthalenesulfonic acid, 1-naphthol-4-sulfonic acid, dodecylsulfonic acid, and oxalic acid. An exemplary catalyst is sulfuric acid or a sulfonic acid, such as p-toluenesulfonic acid (PTSA). A catalyst media can be used for suspending the homogeneous acidic catalyst. For example, surface-active clay minerals such as montmorillonite, hectorite, halloysite, attapulgite, and sepiolite can be used. The amount of the acidic catalyst used in the reaction mixture may range from about 1 wt % to about 20 wt %, or from about 2 wt % to about 10 wt % of the total reactants. When using the acidic catalysts, the amounts of water or moisture content may be minimized to avoid poisoning the catalyst. The amount of water or moisture content may be present to up to 10 wt %, or up to 5 wt %.

The weight ratio of the phenolic compound to the unsaturated fatty acid composition typically ranges from about 2:1 to about 5:1, but can be higher.

In carrying out the above reaction between the phenolic compound and the unsaturated fatty acid, the temperature can range from about 90° C. to about 120° C., from about 90° C. to about 110° C., from about 90° C. to about 105° C., or from about 90° C. to about 100° C. Significantly above this temperature range results in higher ester formation. The reaction can last for from about 1 hour to about 10 hours, or from about 3 hours to about 8 hours.

After the reaction is complete, the acidic catalyst can be neutralized with an aqueous base, such as aqueous sodium hydroxide. The remaining phenolic compound, if any, can be removed by distillation. If a catalyst media is used for suspending the acidic catalyst, the catalyst media is removed prior to distillation. The distillation can be a vacuum distillation, and can be carried out at a temperature ranging from about 120° C. to about 140° C., or about 130° C. These steps further reduce the ester content.

Using the above reaction conditions, the content of the phenolic ester in the resulting phenolic fatty acid compound can be reduced to less than 5 wt %, less than 3 wt % or less than 1 wt %.

Use of Phenolic Fatty Acid Compounds

One aspect of the invention relates to a method for chemically bonding a phenolic resin with a non-phenolic polymer. The method comprises contacting a phenolic fatty acid compound with a non-phenolic polymer having a functional group reactive to a carboxylic acid group of a fatty acid, to react the carboxylic acid-reactive functional group of the non-phenolic polymer with the carboxylic acid group of the phenolic fatty acid compound, thereby attaching a hydroxy phenyl functional group to the non-phenolic polymer. The method further comprises reacting the hydroxy phenyl functional group of the non-phenolic polymer with a phenolic resin or a phenolic crosslinker composition capable of forming a phenolic resin, to chemically bond the phenolic resin with the non-phenolic polymer.

The non-phenolic polymer does not react, or only reacts minimally, with the phenolic resin, without the presence of the phenolic fatty acid compound. The method takes advantage of the bi-functionality of the phenolic fatty acid compound, i.e., the carboxylic acid functionality and the hydroxy phenyl functionality, to chemically bond the non-phenolic polymer phase and the phenolic resin phase.

One aspect of the reaction involves the carboxylic acid group of the phenolic fatty acid compound reacting with a carboxylic acid-reactive functional group within the non-phenolic polymer, e.g., —OR, —COOR, $CH_2$=CHCOOR, —NH, or —CONH, to introduce the hydroxy phenyl functionality from the phenolic fatty acid compound into the non-phenolic polymer. This reaction typically occurs in the presence of a metal-based catalyst or an acidic catalyst.

Suitable metal-based catalysts include, but are not limited to, an antimony-based catalyst such as antimony trioxide, antimony glucoxide, antimony butoxide, acetyl antimony dibutoxide, antimony triacetate; a tin-based catalyst such as dibutyltin oxide (DBTO), dioctyltin oxide (DOTO), mono butylchlorotin dihydroxide, mono butyloxide (MBTO), dibutyltin diacetate (DBTA), dibutyltin maleate dibutyltin dilaurate (DBTL), dioctyltin dilaurate (DOTL), butyltin tris(2-ethylhexanoate), and lauryl stannoxane; a titanium-based catalyst such as alkyl titanate (e.g., titanium tetraisobutoxide, tetraisopropyl titanate, tetra-n-butyl-titanate, tetramethyl titanate, acetyl triisopropyl titanate, tetraisobutyl titanate), titanium alkoxide, titanium tetrachloride, titanyl oxalate and orthotitanic acid; and a co-catalyst of phosphorus and any metal element of beryllium, magnesium, calcium, strontium, barium, boron, aluminum, gallium, tin, manganese, cobalt, zinc, germanium, and antimony; and combinations thereof.

Suitable acidic catalysts include, but are not limited to, a lewis acid; a strong acid catalyst such as one or more sulfonic acids or other strong acids (an acid with a pKa about 3 or less); a triflic acid; a triflate salt of a metal of Group IIA, IIB, IIIA, IIIB, or VIIIA of the Periodic Table of Elements, e.g., the Group IIA metal triflate catalysts such as magnesium triflate, the Group IIB metal triflate catalysts such as zinc and cadmium triflate, the Group IIIA metal triflate catalysts such as lanthanum triflate, the Group IIIB metal triflate catalysts such as aluminum triflate, and the Group VIIIA metal triflate catalysts such as cobalt triflate; a mixture of the triflate salts; and combinations thereof.

The amount of catalysts can range from about 1 ppm to about 10,000 ppm, or from about 10 ppm to about 1,000 ppm, based on the total weight of the reaction mixture. For example, the amount of each metal triflate catalyst can range from about 10 to about 1,000 ppm, or from about 10 to about 200 ppm, based on the total weight of the reaction mixture. A metal triflate catalyst can be used in the form of a solution or in an organic solvent. Exemplary organic solvents include water; alcohols such as n-butanol, ethanol, propanol; aromatic hydrocarbon solvents; cycloaliphatic polar solvents such as cycloaliphatic ketones (e.g. cyclohexanone); polar aliphatic solvents such as alkoxyalkanols, 2-methoxyethanol; non-hydroxyl functional solvents; and mixtures thereof.

The other aspect of the invention involves the hydroxy phenyl functionality of the phenolic fatty acid compound (i.e., the functional group that is being introduced into the non-phenolic polymer) chemically reacting with hydroxymethyl or other methylene donors in the phenolic resin. This reaction results in a covalent bond between the two species.

The reaction typically occurs in the presence of a basic catalyst. Suitable basic catalysts include, but are not limited to, ammonium hydroxide, tertiary amines, alkali and alkaline earth metal oxides and hydroxides, and combinations thereof.

A phenolic fatty acid compound refers to a phenolic compound with the phenol benzene ring alkylated by the aliphatic chains of a fatty acid. The reaction mechanism of the phenolic fatty acid compound formation and suitable reagents for this alkylation reaction, i.e., suitable phenolic compounds and unsaturated fatty acids, have been discussed in the above embodiments. Any phenolic fatty acid compound resulting from the alkylation of the phenolic compound with the unsaturated fatty acid discussed in the above embodiments can be used in this method. Commercially available phenolic fatty acid compound can also be used. Exemplary phenolic fatty acid compounds include hydroxyphenyl stearic acid (e.g., [9,10]-(p-hydroxyphenyl)-octadecanoic acid), hydroxyphenyl oleic acid, hydroxyphenyl linoleic acid, hydroxyphenyl palmitic acid, hydroxyphenyl behenic acid, and combinations thereof. The phenolic fatty acid compound can be used in an amount ranging from about 0.1 wt % to about 50 wt %, for instance, from about 0.1 wt % to about 20 wt %, from about 1 wt % to about 15 wt %, from about 2 wt % to about 10 wt %, from about 5 wt % to about 50 wt %, or from about 5 wt % to about 20 wt % of the non-phenolic polymer. In one embodiment, the phenolic fatty acid compound is hydroxyphenyl stearic acid, and is used in an amount ranging from about 0.1 wt % to about 20 wt %, for instance, from about 1 wt % to about 15 wt %, or from about 2 wt % to about 10 wt % of the non-phenolic polymer.

Non Phenolic Polymers

Suitable non-phenolic polymers include, but are not limited to, a polyester, a polyether, a polyacetate, an acrylic compound, a polyamide, a polyamine, a polysulfone, an epoxy, and combinations thereof. The non-phenolic polymer suitable for use herein contain at least one carboxylic acid-reactive functional group, e.g., an —OR, —COOR, $CH_2$=CHCOOR, —NH, or —CONH, to react with carboxylic acid group of the phenolic fatty acid compound.

The non-phenolic polymers can be prepared by methods known to one skilled in the art. For example, a polyester can be prepared from a diol and a diacid, such that hydroxyl, amine, or glycidyl groups are available to react with the carboxylic acid of the phenolic fatty acid compound. Suitable polyesters include, but are not limited to, polyglycolic acid (PGA) polylactic acid (PLA), polycaprolactone (PCL), polyhydroxyalkanoate (PHA), polyhydroxybutyrate (PHB), polyethylene adipate (PEA), polybutylene succinate (PBS), poly(3-hydroxybutyrate-co-3-hydroxyvalerate) (PHBV), polyethylene terephthalate (PET) (e.g., Mylar® from DuPont), polybutylene terephthalate (PBT), polytrimethylene terephthalate (PTT), polyethylene naphthalate (PEN), and vectran.

Suitable polyethers include, but are not limited to, polyoxymethylene (POM), polyacetal or polyformaldehyde (e.g., Delrin® from DuPont); polyethylene glycol (PEG), or polyethylene oxide (PEO) (e.g., CARBOWAX™ from Dow); polypropylene glycol (PPG) or polypropylene oxide (PPO); polytetramethylene glycol (PTMG) or polytetrahydrofuran (PTHF) (e.g., TERATHANE® from INVISTA); polytetramethylene ether glycol (PTMEG) (e.g., PolyTHF® from BASF); phenyl ether (PPE); and poly(p-phenylene oxide).

Polyacetate typically refers to polyvinyl acetate (PVA). PVA can be prepared by polymerization of vinyl acetate monomer (free radical vinyl polymerization of the monomer vinyl acetate). Suitable polyacetate can also include ethylene vinyl acetate (EVA), and polyvinyl acetate phthalate (PVAP).

Polyacrylic may be prepared from an ethylenically unsaturated monomer component having non-functional ethylenically unsaturated monomers such as butyl acrylate, methyl methacrylate, styrene, benzyl methacrylate, and mixtures thereof; and optionally with lesser amounts of functional monomers such as hydroxy propyl methacrylate, hydroxy ethyl acrylate, glycidyl methacrylate, acrylic acid, methacrylic acid, acetoacetoxy ethyl methacrylate, phosphate esters monomethacrylate and mixtures thereof. In some embodiments, the monomer providing hydroxyl functionality is added at a level up to about 30 wt % of the ethylenically unsaturated monomer component mixture, the monomer providing acid functionality is added at a level up to about 30 wt % of the ethylenically unsaturated monomer component mixture. In some embodiments, acetoacetoxy ethyl methacrylate is added at a level up to about 30 wt % of the ethylenically unsaturated monomer component mixture. Phosphate esters of monomethacrylates (such as Sipomer Pam-100, Pam-200 and Pam-400) can be added at a level up to about 20 wt % of the ethylenically unsaturated monomer component mixture. In some embodiments, about 10 to about 50 wt % of the ethylenically unsaturated monomer component mixture is a monomer having an acid functionality. In some embodiments, the monomer providing an acid functionality is methacrylic acid. In certain embodiments, glycidyl methacrylate is used at levels of about 10 to about 20 wt % of the ethylenically unsaturated monomer component mixture, and the phenolic fatty acid compound, is adducted with the acrylic polymer after it is formed.

The initiator used to polymerize the ethylenically unsaturated monomers may include azo compounds such as 2,2'-azo-bis(isobutyronitrile), 2,2'-azo-bis(2,4-dimethylvaleronitrile), and 1-t-butyl-azocyanocyclohexane); hydroperoxides such as t-butyl hydroperoxide and cumene hydroperoxide; peroxides such as benzoyl peroxide, caprylyl peroxide, di-t-butyl peroxide, ethyl 3,3'-di(t-butylperoxy) butyrate, ethyl 3,3'-di(t-amylperoxy) butyrate, t-amylperoxy-2-ethyl hexanoate, 1,1,3,3-tetramethylbutyl-peroxy-2-ethylhexanoate, and t-butylperoxy pivilate; peresters such as t-butyl peracetate, t-butyl perphthalate, and t-butyl perbenzoate; percarbonates, such as di(1-cyano-1-methylethyl)peroxy dicarbonate, perphosphates, and t-butyl peroctoate; and mixtures thereof. In some embodiments, the initiator is present in an amount from about 0.1 to about 15 wt %, or from about 1 to about 5 wt % of the monomer mixture. In some embodiments, the initiator is added over about 2 hours, simultaneously with the monomers as a feed to a solvent mixture, held at a suitable temperature relative to the half-life of the initiator.

Suitable polyamides include, but are not limited to, aliphatic polyamides, such as PA 6 and PA 66 (e.g., Nylon from DuPont; TECHNYL® from Rhodia; Rilsan® and Rilsamid® from Arkema); polyphthalamides (PPA) (e.g, Trogamid® from Evonik Industries; Amodel® from Solvay); and Aramides (such as Kevlar® and Nomex® from DuPont; Teijinconex, Twaron and Technora from Teijin; Kermel from Kermel; and Spectra® from Honeywell.); as well as mixed aliphatic polyamides/aromatic polyamides. For instance, polyamides can be prepared from reacting diamines, such as ethylene diamine, hexamethylene diamine, piperazine, or mixtures thereof, with diacids, such as isophthalic acid, adipic acid, dimer fatty acids, cyclohexanedioic acid, naphthalenedioic acid, terephthalic acid, or mixtures thereof. Triacids, triols, or any other glycols may be included to provide branching to the polymer (the resulting polymer can be considered as a polyester-amide); and the phenolic fatty acid compound may react with either the amine functionality or the hydroxyl functionality.

Suitable polyamines include, but are not limited to, polyethylene amine, piperazine, cyclen, and cyclam. Polyamine can also be prepared based from ethylene diamine, 1,3-diaminopropane, and hexamethylenediamine.

A typical polysulfone is produced by the reaction of a diphenol and bis(4-chlorophenyl)sulfone, forming a polyether by elimination of sodium chloride. The diphenol is typically bisphenol-A or 1,4-dihydroxybenzene. Suitable polysulfones include, but are not limited to, polysulfones (e.g., Udel®), polyarylsulfones (e.g., Astrel), polyether sulfones (e.g., Ultrason®), or polyarylethesulfones (e.g., VICTREX®).

The non-phenolic polymer can be a synthetic fabric material for utilization as a reinforcing material. Suitable synthetic fabric materials include, but are not limited to, nylon, rayon, polyester, aramid, polysulfone, or other organic and inorganic compositions, as discussed and exemplified in the above embodiments. These synthetic fabric materials may be in the form of, for instance, filaments, fibers, cords, or fabric sheets.

Phenolic Resins

A phenolic resin or a phenolic crosslinker composition capable of forming a phenolic resin is used in the method. Any phenolic compound known in the art suitable for the condensation reaction with one or more aldehydes may be used to prepare the phenolic resin or the phenolic crosslinker composition. The phenolic compound may be a monohydric, dihydric, or polyhydric phenol. Suitable monohydric, dihydric, or polyhydric phenols include, but are not limited to, phenol; dihydricphenols such as resorcinol, catechol, hydroquinone; dihydroxybiphenol; alkylidenebisphenols, such as 4,4'-methylenediphenol (bisphenol F), and 4,4'-isopropylidenediphenol (bisphenol A); trihydroxybiphenol; and thiobisphenols. The benzene ring of the monohydric, dihydric, or polyhydric phenols can be substituted in the ortho, meta, and/or para positions, by one or more linear, branched, or cyclic $C_1$-$C_{30}$ alkyl, or halogen (F, Cl, or Br). For example, the benzene ring can be substituted by $C_1$-$C_6$ alkyl, or $C_1$-$C_4$ alkyl. Exemplary phenolic compounds include phenol or resorcinol; or phenol or resorcinol substituted with one or more methyl groups, such as cresol, xylenol, or methyl resorcinol.

The phenolic resin can be a monohydric, dihydric, or polyhydric phenol-aldehyde resin known to one skilled in the art. The monohydric, dihydric, or polyhydric phenol of the phenol-aldehyde resin is unsubstituted or substituted with one or more linear, branched, or cyclic $C_1$-$C_{30}$ alkyl, or halogen (F, Cl, or Br). Any aldehyde known in the art suitable for phenol-aldehyde condensation reaction may be used to form phenol-aldehyde resins. Exemplary aldehydes include formaldehyde, methylformcel, butylformcel, acetaldehyde, propionaldehde, butyraldehyde, crotonaldehyde, valeraldehyde, caproaldehyde, heptaldehyde, benzaldehyde, as well as compounds that decompose to aldehyde such as paraformaldehyde, trioxane, furfural, hexamethylenetriamine, aldol, β-hydroxybutyraldelhyde, and acetals, and mixtures thereof. A typical aldehyde used is formaldehyde.

The phenolic resin can be prepared by methods known to one skilled in the art. For example, the process for preparing novolak resins can be found in U.S. Pat. Nos. 8,030,418 and 8,470,930, which are hereby incorporated by reference in their entirety; the process for preparing base-modified alklyphenol-aldehyde resins can be found in U.S. Pat. No. 8,030,418, which is hereby incorporated by reference in its entirety.

The phenolic resins can be used in the form of viscous solutions or, when dehydrated, brittle resins with varying softening points capable of liquefying upon heating. The phenolic resin solution can be an aqueous solution, or the phenolic resin can be dissolved in an organic solvent such as alcohols, ketones, esters, or aromatic solvents. Suitable organic solvents include, but are not limited to, n-butanol, acetone, 2-butoxy-ethanol-1, xylene, propylene glycol, N-butyl Cellosolve, diethylene glycol monoethyl ether, and other aromatic solvents or ester solvents, and mixtures thereof.

When employing the method to chemically bond a phenolic resin with a non-phenolic polymer, the non-phenolic polymer modified by the phenolic fatty acid compound can be reacted with the phenolic resin after the phenolic resin is formed.

Alternatively, the non-phenolic polymer modified by the phenolic fatty acid compound can be reacted with a phenolic crosslinker composition before or during the components in the phenolic crosslinker composition react to form the phenolic resin. The phenolic crosslinker composition may comprise a phenolic compound, and/or aldehyde, and any component that can assist in forming a phenolic resin.

Coating Composition

In some embodiments, a coating composition is prepared by reacting a phenolic fatty acid compound, such as a phenol stearic acid compound, a diacid and a diol to produce a hydroxyl phenyl functional polymer, and blending the hydroxyl phenyl functional polymer with a phenolic crosslinker in the presence of a non-aqueous solvent to form the coating composition, wherein the acid number of the hydroxyl phenyl functional polymer is less than about 30 mg KOH/resin.

A monomer component may react with the phenol fatty acid compound to produce a hydroxyl phenyl functional polymer. The polymer may be a polyester, an acrylic compound, a polyamide, an epoxy resin, and the like, or a combination thereof. For example, the polymer may be a polyester prepared from a diol and a diacid, such that hydroxyl, amine, or glycidyl groups are available to react with the carboxylic acid of the phenol fatty acid compound.

The phenolic fatty acid compound operates in the coating composition as described above.

Suitable ethylenically unsaturated monomer components for preparing the hydroxyl phenyl functional polymer, and the initiator used to polymerize the ethylenically unsaturated monomers have been discussed herein.

Epoxidized vegetable oils can be used as the epoxy resin used to form the hydroxyl phenyl functional polymer. Epoxidized vegetable oils can be prepared from vegetable oils by, for example, adding hydrogen peroxide and formic or acetic acid to the vegetable oil, and then holding the mixture at an elevated temperature until some or all of the carbon-carbon double bonds are converted to epoxide groups.

Vegetable oils contain primarily glycerides which are triesters of glycerol and fatty acids with varying degrees of unsaturation. For example, suitable epoxidized vegetable oils can be made from vegetable oils (fatty acid triglycerides) such as esters of glycerol and fatty acids having an alkyl chain of about 12 to about 24 carbon atoms. Fatty acid glycerides which are triglycerides in unsaturated glyceride oils are generally referred to as drying oils or semidrying oils. Drying oils include, for non-limiting example, linseed oil, perilla oil and combinations thereof, while semidrying oils include, without limitation, tall oil, soy bean oil, safflower oil and combinations thereof. Triglyceride oils in some embodiments have identical fatty acid chains or alternatively have different fatty acid chains attached to the same glycerol molecule. In some embodiments, the oils have fatty acid chains containing non-conjugated double bonds. In some embodiments, single double bond or conjugated double bond fatty acid chains are used in minor amounts. Double bond unsaturation in glycerides can be measured by iodine value (number) which indicates the degree of double bond unsaturation in the fatty acid chains. Unsaturated fatty acid glyceride oils employed in some embodiments of the invention have an iodine value greater than about 25 and alternatively between about 100 and about 210.

Naturally occurring vegetable oils for use in the invention can be for non-limiting example, mixtures of fatty acid chains present as glycerides, and include without limitation a distribution of fatty acid esters of glyceride, where the fatty acid distribution may be random but within an established range that may vary moderately depending on the growing conditions of the vegetable source. Soybean oil is employed in some embodiments which comprises approximately about 11% palmitic, about 4% stearic, about 25% oleic, about 51% linolenic, and about 9% linoleic fatty acids, where oleic, linoleic and linolenic are unsaturated fatty acids. Unsaturated vegetable oils employed include without limitation, glyceride oils containing non-conjugated unsaturated fatty acid glyceride esters such as linoleic and linolenic fatty acids.

Unsaturated glyceride oils include, without limitation, corn oil, cottonseed oil, rapeseed oil, hempseed oil, linseed oil, wild mustard oil, peanut oil, perilla oil, poppyseed oil, rapeseed oil, safflower oil, sesame oil, soy bean oil, sunflower oil, canola oil, tall oil, and mixtures thereof. Suitable fatty acid glycerides include, for non-limiting example, those which contain linoleic and linolenic fatty acid chains, oils such as hempseed oil, linseed oil, perilla oil, poppyseed oil, safflower oil, soy bean oil, sunflower oil, canola oil, tall oil, grapeseed oil, rattonseed oil, corn oil, and similar oils which contain high levels of linoleic and linolenic fatty acid glyceride. Glycerides can contain lesser amounts of saturated fatty acids in some embodiments. For example, soy bean oil can be employed which contains predominantly linoleic and linolenic fatty acid glycerides. Combinations of such oils are employed in some embodiments. Vegetable oils can by fully or partially epoxidized by known processes, for example, using acids such as peroxy acid for epoxidation of unsaturated double bonds of the unsaturated vegetable oil. Unsaturated glyceride oils employed in some embodiments include mono-, di-glycerides and mixtures thereof with tri-glycerides or fatty acid esters of saturated and unsaturated fatty acids.

In some embodiments, the epoxidized vegetable oil comprises corn oil, cottonseed oil, grapeseed oil, hempseed oil, linseed oil, wild mustard oil, peanut oil, perilla oil, poppyseed oil, rapeseed oil, safflower oil, sesame oil, soy bean oil, sunflower oil, canola oil, tall oil, a fatty acid ester, monoglyceride or diglyceride of such oils, or a mixture thereof.

Commercially available sources of epoxidized vegetable oils are used in some embodiments, for example, epoxidized soy oil sold under the trade designations "VIKOLOX" and "VIKOFLEX 7170" (Arkema, Inc), "DRAPEX 6.8" (Chemtura Corporation), and "PLAS-CHECK 775" (Ferro Corp.) Other suitable epoxidized vegetable oils include, for on-limiting example, epoxidized linseed oil sold under the trade designations "VIKOFLEX 7190" (Arkema, Inc.) and "DRAPEX 10.4" (Chemtura Corporation), epoxidized cotton seed oil, epoxidized carthamus oil and mixtures thereof. Epoxidized soy bean oil is employed in some embodiments.

In some embodiments, the hydroxyl functional material used to form the hydroxyl functional polymer by reaction with the epoxidized vegetable oil includes, without limitation, propylene glycol, ethylene glycol, 1,3-propane diol, neopentyl glycol, trimethylol propane, diethylene glycol, a polyether glycol, a polyester, a polycarbonate, a polyolefin, a hydroxyl functional polyolefin, and combinations thereof. The hydroxyl functional material includes an alcohol in some embodiments such as n-butanol, 2-ethyl hexanol, benzyl alcohol, or combination thereof with diols or polyols.

Suitable reactions and monomers for preparing polyamides and the resulting hydroxyl phenyl functional polymer have been discussed herein.

The acid number of the hydroxyl phenyl functional polymer is less than about 30 mg KOH/resin ion certain embodiments of the invention. This acid number can improve pigment dispersion, substrate wetting, adhesion and corrosion resistance of the coating composition.

Suitable catalysts for reacting the carboxylic acid group of the phenolic fatty acid compound with a carboxylic acid-reactive functional group to introduce a hydroxyl phenyl functional into the non-phenolic polymer has been described herein.

In some embodiments, the compounds used to form the hydroxyl phenyl functional polymer are heated in the presence of a catalyst and a solvent (such as propylene glycol) to a temperature of about 50 to about 160° C. Optionally, another solvent (such as ethylene glycol monobutyl ether or diethylene glycol monoethyl ether) can be included in the synthesis of the epoxidized vegetable oil and hydroxyl functional material to help control viscosity. Suitable solvents include for non-limiting example, a ketone such as methyl amyl ketone, an aromatic solvent such as xylene or Aromatic 100, an ester solvent or other non-hydroxyl functional solvent, and mixtures thereof. Up to about 90% of a solvent based on the total weight reaction mixture is employed in various embodiments, or about 5 to about 30% is employed. Solvents selected from those described above as well as other solvents including, without limitation, hydroxyl functional solvents can be added upon cooling. In some embodiments, it is desirable to have a final NV (non-volatile content by weight) of about 30 to about 50.

In some embodiments, the hydroxyl phenyl functional polymer is chemically reacted with a phenolic resin or a phenolic crosslinker capable of forming the phenolic resin to form a curable coating composition. Suitable phenolic resins or phenolic crosslinker compositions have been discussed herein. The weight ratio of the phenolic resins or phenolic crosslinkers to the hydroxyl functional phenyl polyester may be from about 10/90 to about 40/60 at about 30-60% solids. The resulting coating composition may provide excellent film performance at very short baking for coil applications.

Optionally, the reaction of the hydroxyl phenyl functional polymer and the phenolic resin or the phenolic crosslinker can occur in the presence of a cure catalyst. Suitable cure catalysts include, for non-limiting example, dodecyl benzene sulfonic acid, p-toluene sulfonic acid, phosphoric acid, and mixtures thereof. In some embodiments, other polymers may be blended into the coating composition, such as polyethers, polyesters, polycarbonates, polyurethanes, and mixtures thereof. Cure conditions for packaging coatings in some embodiments are about 5 to about 60 seconds at about 400° F. to about 600° F., and alternatively about 5 seconds to about 20 seconds at about 400° F. to about 500° F.

The copolymers and the coating compositions can include conventional additives known to those skilled in the art, such as flow agents, surface active agents, defoamers, anti-cratering additives, lubricants, meat-release additives, and cure catalysts.

In some embodiments, one or more coating compositions are applied to a substrate, such as cans, metal cans, easy-open-ends, packaging, containers, receptacles, can ends, or any portions thereof used to hold or touch any type of food or beverage. In some embodiments, one or more coatings are applied in addition to the coating compositions. For example, a prime coat may be applied between the substrate and the coating composition.

The coating compositions can be applied to substrates in any manner known to those skilled in the art. In some embodiments, the coating compositions are sprayed or roll coated onto a substrate.

When applied, the coating compositions contain, for non-limiting example, between about 20 wt % and about 40 wt % of polymeric solids relative to about 60 wt % to about 80 wt % of solvent. For some applications, typically those other than spraying, solvent borne polymeric solutions can contain, for example, between about 20 wt % and about 60 wt % of polymer solids. Organic solvents are utilized in some embodiments to facilitate roll coating or other application methods and such solvents can include, without limitation, n-butanol, 2-butoxy-ethanol-1, xylene, propylene glycol, N-butyl cellosolve, diethylene glycol monoethyl ether and other aromatic solvents and ester solvents, and mixtures thereof. In some embodiments, N-butyl cellosolve is used in combination with propylene glycol. The resulting coating compositions can applied by conventional methods known in the coating industry, for example, spraying, rolling, dipping, coil coating, and flow coating application methods. In some embodiments, after application onto a substrate, the coating composition is thermally cured at temperatures in the range of about 200° C. to about 250° C., or higher, for a time sufficient to effectuate complete curing as well as volatilizing any fugitive components.

The coating compositions can be pigmented and/or opacified with known pigments and opacifiers in some embodiments. For many uses, including, for instance, food use, the pigment can be zinc oxide, carbon black, or titanium dioxide. The resulting coating compositions can be applied by conventional methods known in the coating industry, for example, spraying, rolling, dipping, and flow coating application methods, for both clear and pigmented films. In some embodiments, after application onto a substrate, the coating composition is thermally cured at temperatures in the range of about 130° C. to about 250° C., or higher, for a time sufficient to effectuate complete curing as well as volatilizing any fugitive components.

For substrates intended as beverage containers, the coating can be applied at a rate in the range from about 0.5 msi to about 15 milligrams per square inch of polymer coating per square inch of exposed substrate surface. In some embodiments, the water-dispersible coating is applied at a thickness between about 0.1 msi and about 1.15 msi.

For substrates intended as beverage easy-open-ends, the coating can be applied at a rate in the range from about 1.5 to about 15 milligrams per square inch of polymer coating per square inch of exposed substrate surface. Conventional packaging coating compositions are applied to metal at about 232 to about 247° C. When used as a coating for the easy-open-end of a metal container, the coatings of the invention exhibit resistance to retorted beverages, acidified coffees, and isotonic drinks. In some embodiments, the solids content of the coating composition is greater than about 30% and the coating composition has a viscosity from about 35 to about 200 centipoise at 30% solids or above to produce a film weight of about 6 to about 8 msi (milligrams per square inch) so that over blister is minimized and so that the film can have good chemical resistance, such as aluminum pick-up resistance. Some of the coating compositions of can be used for both inside and outside easy-open-end applications.

Process of Bonding a Phenolic Resin with a Synthetic Fabric Material

Another aspect of the invention relates to a method for chemically bonding a phenolic resin with a synthetic fabric material. The method comprises contacting a phenolic fatty acid compound with a synthetic fabric material to introduce a hydroxy phenyl functional group into the synthetic fabric material. The method further comprises reacting the hydroxy phenyl functional group contained in the synthetic fabric material with a phenolic resin or a phenolic cross-linker composition capable of forming a phenolic resin, to chemically bond the phenolic resin with the synthetic fabric material.

The synthetic fabric material does not react, or only reacts minimally, with the phenolic resin, without the presence of the phenolic fatty acid compound. As discussed in the embodiments above, the method takes advantage of the bi-functionality of the phenolic fatty acid compound, i.e., the carboxylic acid functionality and the hydroxy phenyl functionality, to chemically bond the synthetic fabric and the phenolic resin phase: the carboxylic acid group of the phenolic fatty acid compound can react with a carboxylic acid-reactive functional group within the synthetic fabric material to introduce the hydroxy phenyl functionality from the phenolic fatty acid compound into the synthetic fabric material; while the hydroxy phenyl functionality of the phenolic fatty acid compound (i.e., the functional group that is being introduced into the synthetic fabric material) can chemically react with hydroxymethyl or other methylene donor in the phenolic resin.

The step of contacting the phenolic fatty acid compound with the synthetic fabric material to introduce a hydroxy phenyl functional group into the synthetic fabric material can be carried out by liquefying (e.g., melting) the synthetic fabric material into a molten state; and mixing the molten synthetic fabric material with the phenolic fatty acid compound. This step can also be carried out by dissolving the synthetic fabric material in a solution of the phenolic fatty acid compound (as an aqueous solution or a solution containing an organic solvent), and/or heating.

The hydroxy phenyl functional group can be introduced into the synthetic fabric material by chemically reacting the carboxylic acid group of the phenolic fatty acid compound with a carboxylic acid-reactive functional group of the synthetic fabric material in the presence of suitable catalysts. The chemical reaction mechanism and suitable catalysts used for introducing the hydroxy phenyl functionality into the synthetic fabric material are the same as the reaction mechanism and suitable catalysts for introducing the hydroxy phenyl functionality into the non-phenolic polymer, as discussed in the above embodiments.

Alternatively, the hydroxy phenyl functional group can be introduced into the synthetic fabric material by physically dispersing the phenolic fatty acid compound in the synthetic fabric material. When the molten synthetic fabric materials are mixed with the phenolic fatty acid compound and the mixture are re-solidified, the phenolic fatty acid compound can still be immobilized in the re-solidified synthetic fabric materials through molecular interactions between the phenolic fatty acid compound and the synthetic fabric material phase, such as hydrogen bonding, electrostatic interaction, and/or Van der Waals interactions. Moreover, when the mixture of molten synthetic fabric materials and the phenolic fatty acid compound are re-solidified, certain phenolic fatty acid molecules likely emerge on the surface of the synthetic fabric material through hydrophobic interaction and surface tension, thereby immobilizing some hydroxy phenyl functional groups (from the phenolic fatty acid molecules) on the surface of the synthetic fabric materials.

The resulting synthetic fabric materials, modified by the phenolic fatty acid compound, thus contain hydroxy phenyl functional groups to react with the phenolic resin. The modified synthetic fabric material can be re-solidified into a fabric, depending on the shape or form of the desirable fabric, by methods known to one skilled in the art of making synthetic fabric.

The reaction mechanism and suitable catalysts used for reacting the hydroxy phenyl functionality, introduced into the synthetic fabric material, with the phenolic resin are the same as the reaction mechanism and suitable catalysts for reacting the hydroxy phenyl functionality, introduced into the non-phenolic polymer, with the phenolic resin, as discussed in the above embodiments.

The phenolic fatty acid compounds suitable for utilization in the method are the same as suitable phenolic fatty acid compounds for chemically bonding a phenolic resin with a non-phenolic polymer, as discussed in the above embodiments. Exemplary phenolic fatty acid compounds include hydroxyphenyl stearic acid (e.g., [9,10]-(p-hydroxyphenyl)-octadecanoic acid), hydroxyphenyl oleic acid, hydroxyphenyl linoleic acid, hydroxyphenyl palmitic acid, hydroxyphenyl behenic acid, and combinations thereof. The phenolic fatty acid compound can be used in an amount ranging from about 0.1 wt % to about 20 wt %, for instance, from about 0.5 wt % to about 10 wt %, from about 1 wt % to about 15 wt %, from about 2 wt % to about 10 wt %, from 1 wt % to about 5 wt %, or from about 1 wt % to about 3 wt % of the synthetic fabric material. In one embodiment, the phenolic fatty acid compound is hydroxyphenyl stearic acid, and is used in an amount ranging from about 0.1 wt % to about 20 wt %, for instance, from about 1 wt % to about 15 wt %, or from about 2 wt % to about 10 wt % of the synthetic fabric material.

Any synthetic polymers that can be used as a reinforced material can be used as the synthetic fabric material in the method. Suitable synthetic fabric materials include any polyester, polyether, polyacetate, acrylic compound, polyamide, polyamine, polysulfone, for instance, those that have been discussed as non-phenolic polymers in the above embodiments, and combinations thereof. Typical synthetic fabric materials used include nylon, rayon, polyester, aramid, or polysulfone, as discussed and exemplified in the above embodiments. These synthetic fabric materials may be in the form of, for instance, filaments, fibers, cords, or fabric sheets.

Suitable phenolic resins or phenolic crosslinker compositions for utilization in the method are the same as those phenolic resins or phenolic crosslinker compositions used in the reaction between the non-phenolic polymer and phenolic resin, as discussed in the above embodiments.

The phenolic resins can be used in the form of aqueous, viscous solutions or, when dehydrated, brittle resins with varying softening points and capable of liquefying upon heating. The phenolic resin solution can be an aqueous solution, or the phenolic resin can be dissolved in an organic solvent such as an alcohol, ketone, ester, or aromatic solvent. Suitable organic solvents include, but are not limited to, n-butanol, acetone, 2-butoxy-ethanol-1, xylene, propylene glycol, N-butyl Cellosolve, diethylene glycol monoethyl ether, and other aromatic solvents or ester solvents, and mixtures thereof.

The phenolic resin may further comprise an elastomeric latex. For example, the phenolic resin can be a widely used adhesive—resorcinol formaldehyde latex (RFL). Any latex known to make RFL adhesive can be used. For example, the latex component can be a mixture of SBR (styrene butadiene rubber) and VP (vinyl pyridine) latex (i.e., styrene-butadiene-2-vinyl pyridine latex). The aqueous solutions of RFL can differ in their solids content, pH and viscosity; and selection of these parameters depend on type of fabric and the polymer matrix of the article to be reinforced.

In preparing RFL, the phenolic resin may be pre-formed condensation product between a phenolic compound and one or more aldehydes; and the resorcinol-formaldehyde resin can be mixed with a suitable polymeric latex to form a RFL. Alternatively, a suitable polymeric latex can be pre-mixed with a phenolic crosslinker composition, e.g., a reaction system of resorcinol and formaldehyde, before or during reacting resorcinol with formaldehyde to form resorcinol-formaldehyde resin.

The reaction of the phenolic fatty acid compound-modified synthetic fabric material with the phenolic resin or phenolic crosslinker composition can be performed by various techniques known in the area of forming reinforced material. For example, the phenolic fatty acid compound-modified synthetic fabric material can be soaked or dipped in an aqueous solution of the phenolic resin or the phenolic crosslinker composition, thereby facilitating the chemical bonding of the phenolic resin with the synthetic fabric material.

One exemplary reaction system is modified-RFL dipping technology, where the phenolic fatty acid compound-modified synthetic fabric materials (e.g., various reinforcing fabric sheets, fibers, or cords) are soaked or dipped in the RFL solution.

The process for applying RFL onto the modified synthetic fabric materials is the same as conventional RFL dipping technology. The process basically involves soaking or dipping the modified synthetic fabric materials in a RFL solution, followed by removal of the excess RFL solution on the surface of the modified synthetic fabric materials. When the modified synthetic fabric materials is soaked or dipped in the RFL solution, the modified synthetic fabric materials chemically bond with the RFL through the reaction between the hydroxyphenol functional group contained in the modified synthetic fabric materials with the RFL. This reaction can be carried out in the presence of a basic catalyst in the RFL solution. Suitable basic catalysts include, but are not limited to, ammonium hydroxide, tertiary amines, alkali and alkaline earth metal oxides and hydroxides, and combinations thereof.

Typically, the synthetic fabric material does not react, or reacts only minimally, with the phenolic resin, such as RFL, without the presence of the phenolic fatty acid compound. For instance, polyester yarns, aramid yarns, or fabrics do not contain many reactive functional groups and therefore do not give satisfactory adhesion results to articles to be reinforced (e.g., rubber compound) when treated with conventional RFL dipping technology. The phenolic fatty acid compound-modified synthetic fabric materials, however, contain the hydroxy phenyl functionality that can chemically react with RFL to provide an enhanced bonding and enhanced adhesion between the modified synthetic fabric materials and the RFL.

The RFL-modified synthetic fabric materials can then be treated by drying and/or heating, e.g., using ovens. The resulting reinforced material can be incorporated into an article to be reinforced (e.g., a rubber compound). The adhesion between the reinforced material and the article can be physical interactions or chemical interactions, such as chroman ring and methylene bridge formation. Cured RFL contains a continuous resin phase with particles of latex dispersed throughout this phase. The latex also provides reactive sites which can form covalent bonds to the article (e.g., rubber compound) via conventional sulfur crosslinking.

Another exemplary reaction system is modified-dry bonding adhesion technology, where the phenolic fatty acid compound-modified synthetic fabric materials (e.g., various reinforcing fabric sheets, fibers, or cords) are added to the article that is desired to be reinforced (e.g., a rubber compound). A phenolic crosslinker composition, such as resorcinol or resorcinol-formaldehyde solid resin, is also added to the article, along with a suitable methylene donor. Any suitable methylene donor can be used, including but not limited to, hexamethylenetetramine (HMTA), di-, tri-, tetra-, penta-, or hexa-N-methylol-melamine or their partially or completely etherified or esterified derivatives, for example hexamethoxymethylmelamine (HMMM), or nitromethylpropanol (NMP); oxaolidine or N-methyl-1,3,5-dioxazine. Upon curing the rubber compound, the methylene donor in the rubber compound crosslinks with the phenolic compound or phenolic resin; the phenolic resin reacts with the hydroxyphenol group of the embedded phenolic fatty acid compound-modified reinforcing materials, thereby promoting the adhesion of the rubber to the modified reinforcing materials. Advantageously, this embodiment of the invention avoids the use of RFL, or similar material, altogether.

Reinforcing Applications

In some embodiments, the non-phenolic polymers (such as the synthetic fabric materials) are chemically bonded with the phenolic resin to be used as a reinforced material. The method of the invention further comprises combining the phenolic resin on or in an article to be reinforced, prior to or after the reacting step to chemically bond the phenolic resin with the non-phenolic polymer (e.g., the synthetic fabric materials). The article to be reinforced can be, for instance, a circuit board substrate, a fiberglass, or a rubber composition.

The method employs the phenolic fatty acid compound to modify the reinforcing material, i.e., the non-phenolic polymers, to introduce a hydroxy phenol function group into the reinforcing material, rendering it reactive to the phenolic resin.

The phenolic resin can react with the non-phenolic polymer first, e.g., by contacting the non-phenolic polymer (modified with the phenolic fatty acid) with the phenolic resin, as exemplified above via modified-RFL technology; and then the non-phenolic polymer bonded with the phenolic resin can be combined with (or incorporated into) the article to be reinforced (e.g., circuit board substrate, a fiberglass, or a rubber composition).

Alternatively, the phenolic resin can be combined with (or incorporated into) the article to be reinforced (e.g., circuit board substrate, a fiberglass, or a rubber composition) before or during the non-phenolic polymer (modified with the phenolic fatty acid) is incorporated into the article; then the phenolic resin that is combined with the article can react with the non-phenolic polymer (modified with the phenolic fatty acid) after or during the phenolic resin reacts or interacts with the article, as exemplified above via modified-dry bonding adhesion technology.

By this method, the adhesion between the reinforcing material, i.e., the phenolic fatty acid-modified non-phenolic polymer, and the article to be reinforced can be significantly enhanced (by chemical bonding between the reinforcing material and the phenolic resin, as well as the chemical bonding/strong physical interaction between the phenolic resin and the article).

Fabric-Reinforced Articles

Accordingly, one aspect of the invention relates to a synthetic-fabric reinforced rubber composition. The composition comprises a rubber composition and a synthetic fabric phase. The synthetic fabric phase has been (a) modified by a phenolic fatty acid compound to contain a hydroxy phenyl functional group, and (b) coated with a phenolic resin, wherein the synthetic fabric phase and the coated phenolic resin are chemically bonded through the hydroxy phenyl functional group. The synthetic fabric phase can be used as a reinforced material for the rubber composition.

The rubber composition comprises, besides the reinforced materials, one or more rubber compounds. The rubber compound includes a natural rubber, a synthetic rubber, or a mixture thereof. For instance, the rubber composition is a natural rubber composition.

Alternatively, the rubber composition can be a synthetic rubber composition. Representative synthetic rubbery polymers include diene-based synthetic rubbers, such as homopolymers of conjugated diene monomers, and copolymers and terpolymers of the conjugated diene monomers with monovinyl aromatic monomers and trienes. Exemplary diene-based compounds include, but are not limited to, polyisoprene such as 1,4-cis-polyisoprene and 3,4-polyisoprene; neoprene; polystyrene; polybutadiene; 1,2-vinylpolybutadiene; butadiene-isoprene copolymer; butadiene-isoprene-styrene terpolymer; isoprene-styrene copolymer; styrene/isoprene/butadiene copolymers; styrene/isoprene copolymers; emulsion styrene-butadiene copolymer; solution styrene/butadiene copolymers; butyl rubber such as isobutylene rubber; ethylene/propylene copolymers such as ethylene propylene diene monomer (EPDM); and blends thereof. A rubber component, having a branched structure formed by use of a polyfunctional modifier such as tin tetrachloride, or a multifunctional monomer such as divinyl benzene, may also be used. Additional suitable rubber compounds include nitrile rubber, acrylonitrile-butadiene rubber (NBR), silicone rubber, the fluoroelastomers, ethylene acrylic rubber, ethylene vinyl acetate copolymer (EVA), epichlorohydrin rubbers, chlorinated polyethylene rubbers such as chloroprene rubbers, chlorosulfonated polyethylene rubbers, hydrogenated nitrile rubber, hydrogenated isoprene-isobutylene rubbers, tetrafluoroethylene-propylene rubbers, and blends thereof.

The rubber composition can also be a blend of natural rubber with a synthetic rubber, a blend of different synthetic rubbers, or a blend of natural rubber with different synthetic rubbers. For instance, the rubber composition can be a natural rubber/polybutadiene rubber blend, a styrene butadiene rubber-based blend, such as a styrene butadiene rubber/natural rubber blend, or a styrene butadiene rubber/butadiene rubber blend. When using a blend of rubber compounds, the blend ratio between different natural or synthetic rubbers can be flexible, depending on the properties desired for the rubber blend composition.

Also, the rubber composition may comprise additional materials, such as a methylene donor, one or more additives, one or more other reinforcing materials, and one or more oils. As known to the skilled in the art, these additional materials are selected and commonly used in conventional amounts.

Suitable methylene donors include, for instance, hexamethylenetetramine (HMTA), di-, tri-, tetra-, penta-, or hexa-N-methylol-melamine or their partially or completely etherified or esterified derivatives, for example hexamethoxymethylmelamine (HMMM), oxazolidine or N-methyl-1,3,5-dioxazine, and mixtures thereof.

Suitable additives include, for instance, sulfur, carbon black, zinc oxides, silica, waxes, antioxidant, antiozonants, peptizing agents, fatty acids, stearates, accelerators, curing agents, activators, retarders, a cobalt, adhesion promoters, resins such as tackifying resins, plasticizers, pigments, additional fillers, and mixtures thereof.

Suitable other reinforcing materials include, for instance, glass, steel (brass, zinc or bronze plated), or other organic and inorganic compositions. These reinforcing materials may be in the form of, for instance, filaments, fibers, cords or fabrics.

Suitable oils include, for instance, mineral oils and naturally derived oils. Examples of naturally derived oils include tall oil, linseed oil, and/or twig oil. Commercial examples of tall oil include, e.g., SYLFAT® FA-1 (Arizona Chemicals) and PAMAK 4® (Hercules Inc.). The one or more oils may be contained in the rubber composition, relative to the total weight of rubber compounds in the composition, less than about 5 wt %, for instance, less than about 2 wt %, less than about 1 wt %, less than about 0.6 wt %, less than about 0.4 wt %, less than about 0.3 wt %, or less than about 0.2 wt %. The presence of an oil in the rubber composition may aid in providing improved flexibility of the rubber composition after vulcanization.

The rubber compositions can be vulcanized by using mixing equipment and procedures conventionally employed in the art. Likewise, the final rubber products can be fabricated by using standard rubber curing techniques. The reinforced rubber compounds can be cured in a conventional manner with known vulcanizing agents at about 0.1 to 10 phr. A general disclosure of suitable vulcanizing agents may be found in Kirk-Othmer, Encyclopedia of Chemical Technology (3rd ed., Wiley, New York, 1982) vol. 20, pp. 365 to 468 (particularly "Vulcanization Agents and Auxiliary Materials," pp. 390 to 402), and Vulcanization by A. Y. Coran, Encyclopedia of Polymer Science and Engineering (2nd ed., John Wiley & Sons, Inc. 1989), both of which are incorporated herein by reference. Vulcanizing agents can be used alone or in combination.

When forming a synthetic fabric-reinforced rubber composition, two sheets of the rubber composition, for instance a top sheet and a bottom sheet, can be pressed onto the fabric through techniques known in the art, such as in a calendaring operation, and then cured.

The synthetic fabric-reinforced rubber composition employing the synthetic fabric phase, which is chemically bonded with the coated phenolic resin, exhibits significantly enhanced adhesion between the reinforcing synthetic fabric phase and the rubber compound, and thus can be useful to make a wide variety of products, for instance, tires or tire components such as sidewall, tread (or treadstock, subtread), carcass ply, body ply skim, wirecoat, beadfiller, or overlay compounds for tires. Suitable products also include hoses, power belts, conveyor belts, printing rolls, rubber shoe heels, rubber shoe soles, rubber wringers, automobile floor mats, mud flaps for trucks, ball mill liners, and weather strips.

Another aspect of the invention relates to a synthetic-fabric reinforced article. The synthetic-fabric reinforced article comprises an article containing a phenolic resin, and a synthetic fabric phase. The synthetic fabric phase is modified by a phenolic fatty acid compound to contain a hydroxy phenyl functional group. The synthetic fabric phase and the article are chemically bonded through the hydroxy phenyl functional group. The article can be, for instance, a rubber composition, a circuit board substrate, or a fiberglass.

The articles to be reinforced may have contained phenolic resin to bond the hydroxy phenyl functional group that has been introduced into the synthetic fabric phase. The synthetic fabric phase thus may not need to be combined with a phenolic resin before being combined with the article. For example, a rubber composition can often contain some phenolic resin or phenolic crosslinking composition that is capable of forming a phenolic resin. Circuit board substrates are often produced from phenol formaldehyde resins or other polymeric materials containing phenolic resin. Accordingly, by using the phenolic fatty acid compound to modify the synthetic fabric phase, the application of additional adhesive onto the synthetic fabric phase may not be necessary, as long as the article to be reinforced contain some phenolic resin. The resulting synthetic-fabric reinforced article can still have good adhesion between the reinforcing fabric phase and the polymer matrix phase. Upon combining the phenolic fatty acid compound-modified synthetic fabric phase with the article containing a phenolic resin, the hydroxy phenyl functional group in the synthetic fabric phase can chemically bond with the phenolic resin in the article, under conditions effectively to allow such reaction to happen, e.g., under curing conditions, with suitable catalysts, as discussed in the above embodiments.

Any techniques known to one skilled in the art for molding the synthetic-fabric reinforced article can be used. The synthetic-fabric phase preformed and modified by phenolic fatty acid (and/or phenolic resins) can be in a form of fiber, filament, cord, or fabric sheet, placed on or in a mold, or injected into a mold. The article (polymer matrix without reinforcement, e.g., a rubber compound, a circuit board substrate material, or a fiberglass material) can be similarly placed on or in a mold, or injected into a mold. The mixture in the mold is then cured, leaving the synthetic-fabric reinforced article in the shape created by the mold. Heat and/or pressure are sometimes used to cure the article and improve the quality of the final article.

EXAMPLES

The following examples are given as particular embodiments of the invention and to demonstrate the practice and advantages thereof. It is to be understood that the examples are given by way of illustration and are not intended to limit the specification or the claims that follow in any manner.

Example 1: Preparation of Phenol Stearic Acid 100 parts of phenol and 5 parts of p-toluenesulfonic acid (PTSA) were heated in a glass flask equipped with a stirrer, thermometer, and water cooled condenser arranged to return condensed water to the flask. The reaction mixture was heated to between 90 and 105° C. Over a period of 3 hours, 100 parts of oleic acid were added to the reaction mixture while maintaining 90-105° C. reaction temperature. The reaction was allowed to proceed for 5 hours while checking for unreacted phenol by GC every hour. At the end of 5 hours, 45 parts of 50% caustic solution was loaded slowly to the reaction mixture to neutralize the PTSA. The unreacted phenol was removed by distillation under 40 mm vacuum at a temperature of 130° C. Optionally, to further reduce the residual phenol, 10 pph distilled water was loaded to the reaction mixture and distilled at 130° C. and 40 mm vacuum. The resulting product, recovered in the amount of 135 parts, showed by titration to an acid number of 113.

Although preferred embodiments have been depicted and described in detail herein, it will be apparent to those skilled in the art that various modifications, additions, substitutions, and the like can be made without departing from the spirit of the invention and these are therefore considered to be within the scope of the invention as defined in the claims which follow.

We claim:
1. A process for making a phenolic fatty acid compound having a reduced phenolic ester content, comprising:

providing a fatty acid composition comprising at least one unsaturated fatty acid; and reacting a phenolic compound with the fatty acid composition in the presence of an acidic catalyst at a temperature ranging from about 90° C. to about 105° C., to form the phenolic fatty acid compound, wherein the amount of phenolic ester is less than 5%, and wherein the phenolic fatty acid compound is [9,10]-(hydroxyphenol)-octadecanoic acid.

2. The process of claim 1, further comprising the step of neutralizing the acidic catalyst with an aqueous base.

3. The process of claim 2, wherein the aqueous base is sodium hydroxide.

4. The process of claim 1, further comprising removing the unreacted phenolic compound by distillation at a temperature ranging from about 120° C. to about 140° C.

5. A process for making a phenolic fatty acid compound having a reduced phenolic ester content, comprising:

providing a fatty acid composition comprising at least one unsaturated fatty acid;

reacting a phenolic compound with the fatty acid composition in the presence of an acidic catalyst at a temperature ranging from about 90° C. to about 120° C., to form the phenolic fatty acid compound, wherein the amount of phenolic ester is less than 5%;

neutralizing the acidic catalyst with an aqueous base; and removing the unreacted phenolic compound by distillation.

6. The process of claim 5, wherein distillation is effected at a temperature ranging from about 120° C. to about 140° C.

7. The process of claim 5, wherein the acidic catalyst is selected from the group consisting of sulfuric acid, ethanesulfonic acid, benzenesulfonic acid, benzenedisulfonic acid, chlorobenzenesulfonic acid, 3,4-dichlorobenzene sulfonic acid, cresolsulfonic acids, phenol sulfonic acids, toluenesulfonic acids, xylenesulfonic acids, octylphenolsulfonic acid, naphthalenesulfonic acid, 1-naphthol-4-sulfonic acid, dodecylsulfonic acid, and oxalic acid.

8. The process of claim 5, wherein the acidic catalyst is a sulfonic acid.

9. The process of claim 5, wherein the amount of acid catalyst in the reaction mixture ranges from about 2 wt % to about 10 wt % of the total reactants.

10. The process of claim 5, wherein the amount of water or moisture present in the acid catalyst is less than 5 wt %.

11. The process of claim 5, wherein the phenolic compound is a monohydric, dihydric, or polyhydric phenol, with the phenol benzene ring unsubstituted or substituted by one or more linear, branched, or cyclic $C_1$-$C_{30}$ alkyl, or halogen.

12. The process of claim 11, wherein the phenolic compound is selected from the group consisting of phenol, resorcinol, catechol, hydroquinone, dihydroxybiphenol, 4,4'-methylenediphenol (bisphenol F), 4,4'-isopropylidenediphenol (bisphenol A), and trihydroxybiphenol.

13. The process of claim 12, wherein the phenolic compound is phenol, resorcinol, cresol, xylenol, or methyl resorcinol.

14. The process of claim 5, wherein the fatty acid composition is derived from a natural oil selected from the group consisting of soybean oil, peanut oil, walnut oil, palm oil, palm kernel oil, wheat germ oil sesame oil, sunflower oil, safflower oil, rapeseed oil, linseed oil, flax seed oil, colza oil, coconut oil, corn oil, cottonseed oil, olive oil, castor oil, false flax oil, hemp oil, mustard oil, radish oil, ramtil oil, rice bran oil, salicornia oil, tigernut oil, tung oil and mixtures thereof; a fat selected from the group consisting of beef fat, mutton fat, beef tallow, mutton tallow, pork fat, pork lard, turkey fat, chicken fat, duck fat, fish fat, and combinations thereof; or a commercially available oil selected from the group consisting of cotton oil, soy oil, linseed oil, tall oil, and mixtures thereof.

15. The process of claim 5, wherein the unsaturated fatty acid is selected from the group consisting of oleic acid, linoleic acid, linolenic acid, undecylenic acid, palmitoleic acid, erucic acid, isomeric modifications of these acids, and combinations thereof.

16. The process of claim 5, wherein the reacting step involves alkylating the phenolic compound with the fatty acid composition, wherein the reaction occurs at the double bond of the fatty acid and adds a phenol benzene ring and a hydrogen atom to each unsaturated carbon atom of the double bond in the fatty acid.

17. The method of claim 5, wherein the weight ratio of the phenolic compound to the unsaturated fatty acid composition ranges from about 2:1 to about 5:1.

18. The method of claim 5, wherein the reaction between the phenolic compound and the unsaturated fatty acid takes place at a temperature ranging from about 90° C. to about 100° C.

19. The method of claim 5, wherein the reaction between the phenolic compound and the unsaturated fatty acid takes place for about 3 hours to about 8 hours.

20. The method of claim 5, wherein the phenolic fatty acid compound is [9,10]-(hydroxyphenol)-octadecanoic acid, phenol palmitic acid, or phenol behenic acid.

21. The method of claim 5, wherein the content of the phenolic ester in the resulting phenolic fatty acid compound is less than 3 wt %.

22. The method of claim 21, wherein the content of the phenolic ester in the resulting phenolic fatty acid compound is less than 1 wt %.

* * * * *